United States Patent [19]

Janitschke et al.

[11] 4,358,614
[45] Nov. 9, 1982

[54] PREPARATION OF α- AND β-CYCLOCITRAL, AND THE N-METHYLALDIMINES OF THESE COMPOUNDS

[75] Inventors: Lothar Janitschke, Ludwigshafen; Werner Hoffmann, Neuhofen, both of Fed. Rep. of Germany

[73] Assignee: BASF Aktiengesellschaft, Ludwigshafen, Fed. Rep. of Germany

[21] Appl. No.: 279,802

[22] Filed: Jul. 2, 1981

[30] Foreign Application Priority Data

Jul. 22, 1980 [DE] Fed. Rep. of Germany ....... 3027689

[51] Int. Cl.³ .................. C07C 119/00; C07C 45/00
[52] U.S. Cl. .................. 564/248; 564/279; 568/447
[58] Field of Search .................. 568/447, 351, 349; 564/248, 279

[56] References Cited

U.S. PATENT DOCUMENTS 3,365,481 1/1968 Wittig et al. .................. 564/248 X

FOREIGN PATENT DOCUMENTS 44-24107 10/1969 Japan .................. 564/248
7013942 3/1971 Netherlands .................. 564/279

OTHER PUBLICATIONS

Henbest et al., Jour. Chem. Soc. (London) (1952), 1154–1159.

Gedye et al., Can. Jour. Chem., vol. 49 (1971), 1764–1766.

Colombi et al., Helv. Chim. Acta, vol. 28 (1951), 265–273.

*Primary Examiner*—Bernard Helfin
*Attorney, Agent, or Firm*—Oblon, Fisher, Spivak, McClelland & Maier

[57] ABSTRACT

An improved process for the preparation of cyclocitrals of the general formula I

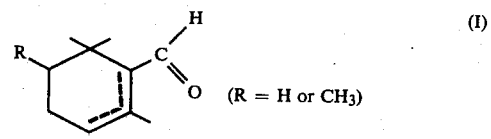

(R = H or $CH_3$)

via the novel N-methylaldimines of the general formula II

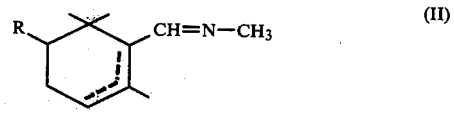

and the novel N-methylaldimines of the formula II. The cyclocitrals of the formula I are obtained in yields of 80–90%, based on citral employed. The compounds I and II are important intermediates for the preparation of fragrances and carotinoids, such as vitamin A, and products related thereto.

6 Claims, No Drawings

PREPARATION OF α- AND β-CYCLOCITRAL, AND THE N-METHYLALDIMINES OF THESE COMPOUNDS

The present invention relates to an improved process for the preparation of cyclocitrals of the general formula I

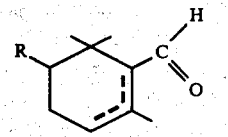

where R is hydrogen or methyl and where the bonds shown in broken lines indicate the presence of a double bond in the 1- or 2-position of the cyclohexene ring.

The invention further relates to the N-methylaldimines of these cyclocitrals, which arise as intermediates and have the general formula II

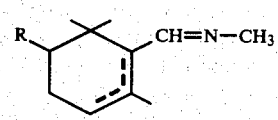

German Pat. No. 123,747 discloses a process for the preparation of cyclocitrals, wherein citral is condensed with aniline or ethylamine and the condensate obtained is cyclized with concentrated acid.

According to a more recent publication (Helv. Chim. Acta, 28, (1951), 264-273), citral is condensed with aniline and the resulting citralanil is condensed with sulfuric acid. This publication states that the method of the above German patent gives yields of only a few percent, but that the yields can be increased to 60-70% if the citralanil is diluted with ether when carrying out the cyclization, and the latter is effected at −15° C., using sulfuric acid containing a little water.

Can. J. Chem. 49 (1971), 1764-1766 also describes a process wherein β-cyclocitral is obtained by condensing citralanil with sulfuric acid. The yields are 50-60%, based on citral employed.

The yields obtainable by the conventional methods are however still unsatisfactory for industrial purposes. It is an object of the present invention to make the cyclocitrals I, which are important compounds for numerous organic syntheses, available more economically, and in higher yields, than the prior art allows.

We have found, surprisingly, that this object is achieved and that the cyclocitrals of the general formula I

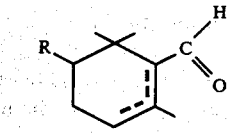

where R is hydrogen or methyl and where the bonds shown in broken lines indicate the presence of a double bond in the 1- or 2-position of the cyclohexene ring, are obtained in a very advantageous manner when an open-chain aldehyde of the general formula III

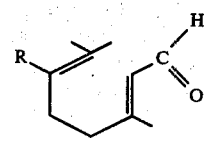

is reacted with methylamine at from −20° to 60° C., preferably from 0° to 40° C., to give its N-methylaldimine, the latter is cyclized at from −30° to 30° C., preferably from −20° to 0° C., with a multi-molar excess of concentrated sulfuric acid, to give the cyclocitral N-methylaldimine of the general formula II

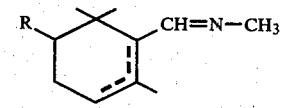

and the last-mentioned compound, with or without intermediate isolation from its reaction mixture, is hydrolyzed to the cyclocitral I in a conventional manner.

Using the process according to the invention, the cyclocitrals are obtained in yields of 80-90%, based on citral employed. This exceptionally good result is surprising since it is known that citral itself cannot be cyclized in this way, because the citral-N-methylaldimines are very easily decomposed (cf. Ber. Dtsch. Chem. Ges. 61 (1928), 1452), and, presumably for this reason, the method chosen hitherto has always been via the substantially more expensive citralanil.

Both the cis-form and the trans-form of III are suitable starting compounds, so that, for example, the cis-trans-isomer mixtures of citral, or the mixtures of the corresponding 6-methyl homologs (hereafter referred to as methylcitral) can be employed.

To prepare the N-methylaldimines, one mole of III is reacted with 2 moles of methylamine, advantageously at room temperature or slightly elevated temperature, ie. from about 20° to 50° C. Thereafter, the aqueous phase formed is separated off, and the excess methylamine is removed by distillation at about 20°-50° C. under a pressure of 10-20 mbar.

The crude N-methylaldimine which is obtained in virtually quantitative yield by this method is then cyclized by dripping it into concentrated sulfuric acid at from −20° to 0° C. The sulfuric acid can contain up to about 10% by weight of water. However, the best results are achieved with concentrated sulfuric acid. The molar ratio of aldimine to sulfuric acid (taken at 100% strength) is in general from 1:2 to 1:10, preferably from 1:4 to 1:7.

Both the preparation of the aldimine of the compound III and its cyclization to the compound of the formula II can be carried out in the presence of a solvent, such as diethyl ether or hexane. However, it is an advantage of the process according to the invention that virtually the same yield is achieved without a solvent.

To isolate the cyclic compound of the formula II, the sulfuric acid solution obtained from the cyclization reaction is neutralized at a relatively low temperature, namely from about −20° to 40° C., so as to suppress the hydrolysis of the Schiff base to the aldehyde. It is advisable first to add about an equal amount of ice to the sulfuric acid solution, and then to neutralize the aqueous acidic solution thus obtained. Very cheap bases, such as sodium hydroxide solution, are used for the neutralization. The cyclocitral α-methylaldimine can be isolated from the neutral or slightly alkaline aqueous solution in a conventional manner, for example by steam distillation, by extraction with a solvent, such as diethyl ether, methyl tert.-butyl ether, n-hexane or toluene, or by means of a combination of both methods.

The cyclocitral N-methylaldimines of the formula II are obtained in the form of mixtures of the 1-ene and 2-ene isomers, ie. as derivatives of α- and β-cyclocitral or of their methyl homologs defined above, the yields being 265–75%, based on citral employed.

To prepare a cyclocitral of the formula I, it is not necessary to isolate the aldimine from its sulfuric acid solution. Rather, it is advantageous to neutralize the solution at an elevated temperature—about 20°–80° C., preferably 30°–50° C.—only to the point that the solution remains slightly acidic and has a pH of from 2 to 6, preferably from 3 to 6. Under these conditions the Schiff base hydrolyzes completely, if necessary after a further period of heating, to give the free aldehyde.

The working up to obtain the cyclocitral is carried out in a conventional manner by steam distillation or by extraction with diethyl ether, methyl t-butyl ether or n-hexane.

The isomer mixture of the 2-ene and 1-ene compounds (α- and β-cyclocitral) is thus obtained in yields of from about 80 to 90%, based on compound III employed. Separation of the isomers by fractional distillation under 0.1–20 mbar is relatively simply achieved.

The ratio of 1-ene- to 2-ene-cyclocitral can be influenced by the working-up conditions. At from −20° to 40° C., especially from 0° to 30° C., and in slightly acidic solution (pH 3.5), a ratio of 1-ene compound to 2-ene compound of from about 40:60 to 20:80 is obtained. If on the other hand the cyclization mixture is worked up without neutralizing by pouring it onto ice and steam-distilling the strongly acidic mixture, the ratio is from 80:20 to 85:15, but in that case significant amounts (about 10–15%) of the re-arrangement products 1-acetyl-4,4-dimethyl- and 1-acetyl-4,4,5-trimethyl-cyclohex-1-ene can form.

The preparation of the cyclocitrals by the process according to the invention can be carried out continuously or batchwise.

The cyclocitrals of the formula I are important intermediates for the preparation of fragrances and carotinoids, such as vitamin A, and products related thereto. The same is true of the N-methylaldimines of the formula II, which resemble the free aldehydes in their reactive behavior and can therefore frequently be further converted direct, ie. without first having to be isolated. Further important synthesis possibilities are the hydrogenations of compounds of the formulae I and II, leading to the corresponding alcohols and amines respectively.

Using the process according to the invention it is possible to prepare cyclocitrals, their methyl homologs and the Schiff bases of these compounds in good yields and high purity.

EXAMPLE 1

(a) Preparation of citral N-methylaldimine 94 g (about 3 moles) of methylamine were passed into 310 g (about 2 moles) of citral (in the form of the commercial cis-trans isomer mixture) in the course of 45 minutes at 20°–25° C., during which an aqueous phase separated out. After a further 10 minutes, the aqueous phase was substantially separated off (about 37 g of aqueous phase being obtained) and the organic residue was partially freed from excess methylamine at 20° C. and 20 mbar. The yield of citral N-methylaldimine was virtually quantitative.

(b) Cyclization of citral N-methylaldimine

The crude citral N-methylaldimine prepared according to Example 1a was dripped into 1,000 g of concentrated sulfuric acid in the course of one hour under a nitrogen atmosphere, at from −10° to −15° C., with vigorous stirring, and after the addition stirring was continued for 20 minutes at −15° C.

(c) Preparation of cyclocitral 1.2 kg of ice were first added to the reaction mixture, containing sulfuric acid, obtained from Example 1b, and then sufficient 50% strength by weight sodium hydroxide solution was added at 40° C. to give a pH of about 3.5. The pH rose to 6.8 in the course of one hour, without addition of further sodium hydroxide solution. The mixture was then brought to pH 7, after which the aqueous phase and the sodium sulfate which had crystallized out were separated off. The organic phase was then steam-distilled and the cyclocitral was extracted from the condensate (about 5 liters) by three extractions, each with 250 ml of diethyl ether. The ether solution was dried and the ether removed, leaving 270.1 g of cyclocitral mixture. This corresponded to a yield of 86%, based on citral employed.

According to an analysis by gas chromatography, the cyclocitral mixture consisted of 62% by weight of a α-cyclocitral, 36% by weight of β-cyclocitral and 2% of compounds not determined in more detail. The isomer mixture was separated by fractional distillation into pure α-cyclocitral (boiling point 39° C./0.4 mbar) and pure β-cyclocitral (boiling point 51°–52° C./0.2 mbar).

EXAMPLE 2

Preparation of α-cyclocitral N-methylaldimine (2,6,6-trimethylcyclohex-2-ene-1-carboxaldehyde N-methylaldimine)

Crude citral N-methylaldimine (347 g) prepared as described in Example 1a was dissolved in 300 ml of n-hexane and cyclized with 1.2 kg of concentrated sulfuric acid under the conditions described in Example 1b. The sulfuric acid mixture was then poured onto 2 kg of ice and neutralized with 50% strength by weight potassium hydroxide solution at 0°–10° C. (using external cooling with solid carbon dioxide/acetone). The organic phase was extracted 3 times with 100 ml of n-hexane at a time. The combined organic phases were worked up in a conventional manner, and on fractional distillation the cyclocitral N-methylaldimine was obtained in 59% yield, based on citral employed. Boiling point 38° C./0.3 mbar.

According to analysis by gas chromatography, the product consisted of 85% by weight of α-cyclocitral N-methylaldimine and 13% by weight of α-cyclocitral.

EXAMPLE 3

Preparation of a product consisting predominantly of α-cyclocitral (2,6,6-trimethylcyclohex-2-ene-1-carboxaldehyde)

50% strength by weight aqueous sulfuric acid was added to 282 g of α-cyclocitral N-methylaldimine at 10°–25° C., until the mixture had a pH of 3.5. After having been stirred for 12 hours at room temperature, the mixture was neutralized with 10% strength by weight sodium hydroxide solution, steam-distilled and worked up as described in Example 1c. 200.3 g of cyclocitral were obtained, corresponding to a yield of 81.2%. According to analysis by gas chromatography, this mixture contained 79% of α-cyclocitral and 20% of β-cyclocitral.

EXAMPLE 4

Preparation of methyl-α-cyclocitral N-methylaldimine (2,5,6,6-tetramethyl-cyclohex-2-ene-1-carboxaldehyde N-methylaldimine)

47 g (1.5 moles) of methylamine were passed into 200 g (1 mole) of 3,6,7-trimethyl-octa-2,6-dien-1-al (not less than 83% pure) over 60 minutes at 20°–25° C., after which the mixture was stirred for 30 minutes at room temperature. The aqueous phase was separated off and the organic phase was freed from excess methylamine on a rotary evaporator (20° C./20 mbar). 195 g of the crude aldimine remained. 450 g of concentrated sulfuric acid were added to this, similarly to Example 1b, and the mixture was then poured onto 3 kg of ice. 1 liter of n-hexane was then added and the aqueous-organic mixture was neutralized with 50% strength by weight sodium hydroxide solution at 0°–5° C., after which the aldimine was isolated similarly to Example 2. 108 g of product were obtained, corresponding to a yield of 60%. (Boiling point = 50° C./0.6 mbar, 96° C./17 mbar).

EXAMPLE 5

Preparation of a product consisting predominantly of 5-methyl-α-cyclocitral (2,5,6,6-tetramethylcyclohex-2-ene-1-carboxaldehyde)

43 g of 2,5,6,6-tetramethylcyclohex-2-ene-1-carboxaldehyde N-methylaldimine were suspended in 50 ml of water and the reaction mixture was brought to pH 2.5 with 50% strength sulfuric acid and then stirred for 30 minutes to 30°–45° C. Thereafter it was brought to pH 7.0 with 50% strength sodium hydroxide solution at 30°–45° C., and extracted with 100 ml of n-hexane. The organic phase was dried with anhydrous sodium sulfate and the solvent was distilled off at 40° C./20 mbar.

Distillation of the crude product thus obtained gave 31.6 g of 5-methylcyclocitral as a cis-trans isomer mixture, corresponding to a yield of 77%. According to analysis by gas chromatography, the product contained 71% of the α-isomer (boiling point 40°–43° C./0.3 mbar) and 16% of the β-isomer.

EXAMPLE 6

Preparation of a product consisting predominantly of 5-methyl-β-cyclocitral (2,5,6,6-tetramethylcyclohex-1-ene-1-carboxaldehyde)

16.6 g of 5-methyl-α-cyclocitral were added dropwise, at 0°–5° C., to a solution of 6.4 g of KOH in 110 ml of methanol, after which the reaction mixture was kept for 80 minutes at 0°–5° C. It was then poured onto 250 ml of ice water and the mixture was saturated with sodium chloride and extracted 5 times with 50 ml of ether at a time. The combined extracts were washed twice with 50 ml of saturated sodium chloride solution at a time, and were dried with anhydrous sodium sulfate.

The solvent was distilled off at 40° C./20 mbar. 14 g of crude product were obtained, containing, according to the H-NMR spectrum, about 5% of the α-isomer and 95% of the β-isomer (boiling point 64°–70° C./0.3 mbar), corresponding to a yield of 84%.

EXAMPLE 7

Preparation of a mixture of α-cyclocitral N-methylaldimine and β-cyclocitral N-methylaldimine by isomerizing α-cyclocitral N-methylaldimine 17 ml of a 30% strength solution of sodium methylate in methanol were added dropwise to a solution of 10 g of α-cyclocitral N-methylaldimine in 100 ml of anhydrous methanol at 0° C. Stirring was continued for 2 hours at 0° C., 100 ml of n-hexane were then added and the mixture was poured onto 500 g of ice water.

The organic phase was separated off and the aqueous phase was extracted 3 times with 50 ml of n-hexane at a time. The combined extracts were washed twice with 250 ml of n-hexane at a time, and dried.

After removing the solvent, 7.5 g of an oil remained, consisting, according to the H-NMR spectrum, of about 75% of α-cyclocitral N-methylaldimine, 15% of β-cyclocitral N-methylaldimine and 5% each of α-cyclocitral and β-cyclocitral.

We claim:

1. A process for the preparation of a cyclocitral of the general formula I

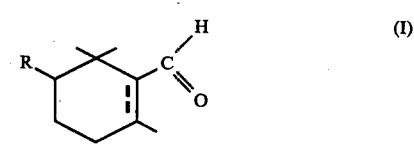

where R is hydrogen or methyl and where the bonds shown in broken lines indicate the presence of a double bond in the 1- or 2-position of the cyclohexene ring, in which an open-chain aldehyde of the general formula III

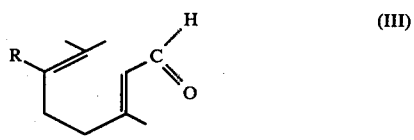

is reacted with methylamine at a suitable temperature to give its N-methylaldimine, the latter is cyclized at a suitable temperature with a multi-molar excess of concentrated sulfuric acid within the range of 1:2 to 1:10, to give the cyclocitral N-methylaldimine of the general formula II

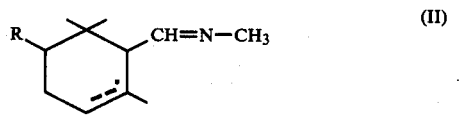

and the last-mentioned compound, with or without intermediate isolation from its reaction mixture, is hydrolyzed to the cyclocitral I in a conventional manner.

2. Cyclocitral N-methylaldimines of the general formula II

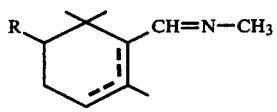

where R is hydrogen or methyl and where the bonds shown in broken lines indicate the presence of a double bond in the 1- or 2-position of the cyclohexene ring.

3. The process of claim 1, wherein α-cyclocitral N-methyl-aldimine is hydrolyzed to obtain a mixture of α-cyclocitral and β-cyclocitral.

4. The process of claim 1, wherein methyl-β-cyclocitral N-methyl-aldimine is hydrolyzed to yield 5-methyl-β-cyclocitral.

5. The product of claim 2, wherein the methylaldimine produced is methyl-α-cyclocitral N-methylaldimine.

6. The product of claim 2, wherein the methylaldimines comprise a mixture of α-cyclocitral N-methylaldimine and β-cyclocitral N-methyl-aldimine.

* * * * *

UNITED STATES PATENT AND TRADEMARK OFFICE
CERTIFICATE OF CORRECTION

PATENT NO. : 4,358,614

DATED : November 9, 1982

INVENTOR(S) : Lothar Janitschke et al.

It is certified that error appears in the above-identified patent and that said Letters Patent is hereby corrected as shown below:

On the title page Item [54] should read:

[54] -- Preparation of Alpha and Beta Cyclocitral, and the N-Methyl-Aldimines of these Compounds --

Signed and Sealed this

Twenty-fourth Day of May 1983

[SEAL]

Attest:

DONALD J. QUIGG

Attesting Officer  Acting Commissioner of Patents and Trademarks